United States Patent
Pringle et al.

(10) Patent No.: US 11,471,235 B2
(45) Date of Patent: Oct. 18, 2022

(54) SURGICAL TABLE DISPOSABLE BASE COVER

(71) Applicant: Trumpf Medizin Systeme GmbH & Co. KG, Saalfeld (DE)

(72) Inventors: Justine Pringle, Grand Rapids, MI (US); Ryan S. Severns, Plainwell, MI (US)

(73) Assignee: Trumpf Medizin Systeme GmbH & Co. KG, Saalfeld (DE)

(*) Notice: Subject to any disclaimer, the term of this patent is extended or adjusted under 35 U.S.C. 154(b) by 105 days.

(21) Appl. No.: 16/800,794

(22) Filed: Feb. 25, 2020

(65) Prior Publication Data
US 2020/0268467 A1 Aug. 27, 2020

Related U.S. Application Data

(60) Provisional application No. 62/810,073, filed on Feb. 25, 2019.

(51) Int. Cl.
*A61B 50/00* (2016.01)
*A61G 13/10* (2006.01)
*A61B 17/00* (2006.01)

(52) U.S. Cl.
CPC .............. *A61B 50/00* (2016.02); *A61G 13/10* (2013.01); *A61B 2017/0023* (2013.01);
(Continued)

(58) Field of Classification Search
CPC .............. A61B 50/00; A61B 2050/002; A61B 2050/0079; A61B 2050/0085;
(Continued)

(56) References Cited

U.S. PATENT DOCUMENTS

| | | | | |
|---|---|---|---|---|
| 2,705,519 A | * | 4/1955 | Kaiser | E03D 1/006 |
| | | | | 4/251.2 |
| 3,185,197 A | * | 5/1965 | Spiro | A47C 31/10 |
| | | | | 150/154 |

(Continued)

FOREIGN PATENT DOCUMENTS

| | | |
|---|---|---|
| CN | 204274924 U | 4/2015 |
| EP | 0481241 A1 | 4/1992 |

(Continued)

OTHER PUBLICATIONS

Resilite, Vault Anchor Mats, Accessed from the Internet at https://www.resilite.com/store/vault-anchor-mats on Dec. 19, 2018.

(Continued)

*Primary Examiner* — Myles A Throop
(74) *Attorney, Agent, or Firm* — Price Heneveld LLP

(57) ABSTRACT

A disposable base cover includes a first portion and a second portion. The first portion includes a top wall and a peripheral side wall extending orthogonally therefrom. The first portion also includes a side edge with a first fastening feature. The second portion includes a top wall and a peripheral side wall extending generally orthogonally therefrom. The second portion also includes an equipment zone that provides visual indicia of equipment zone bounds. The second portion includes a side edge with a second fastening feature that is complementary to the first fastening feature. The disposable base cover is configured for engagement with a base of a surgical table having rollers to provide mobility to the surgical table.

16 Claims, 10 Drawing Sheets

(52) U.S. Cl.
CPC . *A61B 2050/002* (2016.02); *A61B 2050/0079* (2016.02); *A61B 2050/0085* (2016.02)

(58) Field of Classification Search
CPC . A61B 2017/0023; A61B 46/40; A61B 46/10; A61B 46/00; A61G 13/10
See application file for complete search history.

(56) References Cited

U.S. PATENT DOCUMENTS

| | | | | |
|---|---|---|---|---|
| 3,295,577 | A * | 1/1967 | Danielson | A47B 13/086 |
| | | | | 108/90 |
| 4,266,663 | A * | 5/1981 | Geraci | A61B 46/10 |
| | | | | 206/305 |
| 4,991,242 | A | 2/1991 | Brown | |
| 5,339,748 | A * | 8/1994 | Bilotti | A47G 11/004 |
| | | | | 108/90 |
| 5,396,672 | A * | 3/1995 | Brown | A47G 9/0238 |
| | | | | 5/484 |
| 6,105,578 | A * | 8/2000 | Sommers | A61B 46/10 |
| | | | | 128/849 |
| 8,490,846 | B1 * | 7/2013 | Wheatley | B60R 7/06 |
| | | | | 224/483 |
| 9,233,042 | B1 * | 1/2016 | Freude | A61G 13/10 |
| 9,283,041 | B2 * | 3/2016 | Adams | A61B 46/10 |
| 9,707,040 | B2 | 7/2017 | Lager | |
| 10,070,924 | B2 | 9/2018 | Lother et al. | |
| 10,881,478 | B1 * | 1/2021 | Genova | A61B 46/40 |
| 2003/0056698 | A1 * | 3/2003 | Comeaux | A47G 11/004 |
| | | | | 108/90 |
| 2005/0189005 | A1 * | 9/2005 | Smith | G09F 23/00 |
| | | | | 135/16 |
| 2006/0152345 | A1 * | 7/2006 | Aitkenhead | C09J 7/38 |
| | | | | 340/384.1 |
| 2008/0149112 | A1 * | 6/2008 | Levernier | A61B 46/23 |
| | | | | 128/853 |
| 2011/0247634 | A1 * | 10/2011 | Young | A61B 46/00 |
| | | | | 128/849 |
| 2015/0114404 | A1 * | 4/2015 | Czop | A61B 46/10 |
| | | | | 128/856 |
| 2015/0238264 | A1 | 8/2015 | Kerns et al. | |
| 2015/0366618 | A1 | 12/2015 | Higuchi et al. | |
| 2017/0086934 | A1 * | 3/2017 | Devengenzo | A61B 46/23 |
| 2017/0258542 | A1 | 9/2017 | Grenier | |
| 2018/0132660 | A1 * | 5/2018 | Suchevits | A23B 4/052 |
| 2018/0356090 | A1 | 12/2018 | Baldwin | |
| 2019/0099232 | A1 * | 4/2019 | Soto | A61B 46/10 |
| 2019/0328476 | A1 * | 10/2019 | Thompson | A61B 6/4423 |
| 2020/0060780 | A1 * | 2/2020 | Bemman | A61B 46/10 |
| 2020/0128969 | A1 * | 4/2020 | Strasser | A47C 1/11 |
| 2020/0405427 | A1 * | 12/2020 | Genova | A61B 46/40 |
| 2021/0128091 | A1 * | 5/2021 | Youd | A61B 46/40 |
| 2021/0153965 | A1 * | 5/2021 | Lau | A61B 34/30 |

FOREIGN PATENT DOCUMENTS

| | | |
|---|---|---|
| JP | 2012205895 A | 10/2012 |
| WO | 2017143066 A1 | 8/2017 |

OTHER PUBLICATIONS

Rakuten Commerce LLC, Duraviva Outdoor Patio Umbrella Base Stand Weatherproof Layover Cover—Waterproof, Easy-to-Use Quick Fastener Design, Accessed from the Internet at https://www.rakuten.com/shop/ezl-direct/product/DV-UBWPC-1012/ on Dec. 19, 2018.

Dazian, Pipe & Base, "Base Plate Cover," p. 3, Accessed from the Internet at https://www.dazian.com/hardware/pipes-base on Dec. 19, 2018.

\* cited by examiner

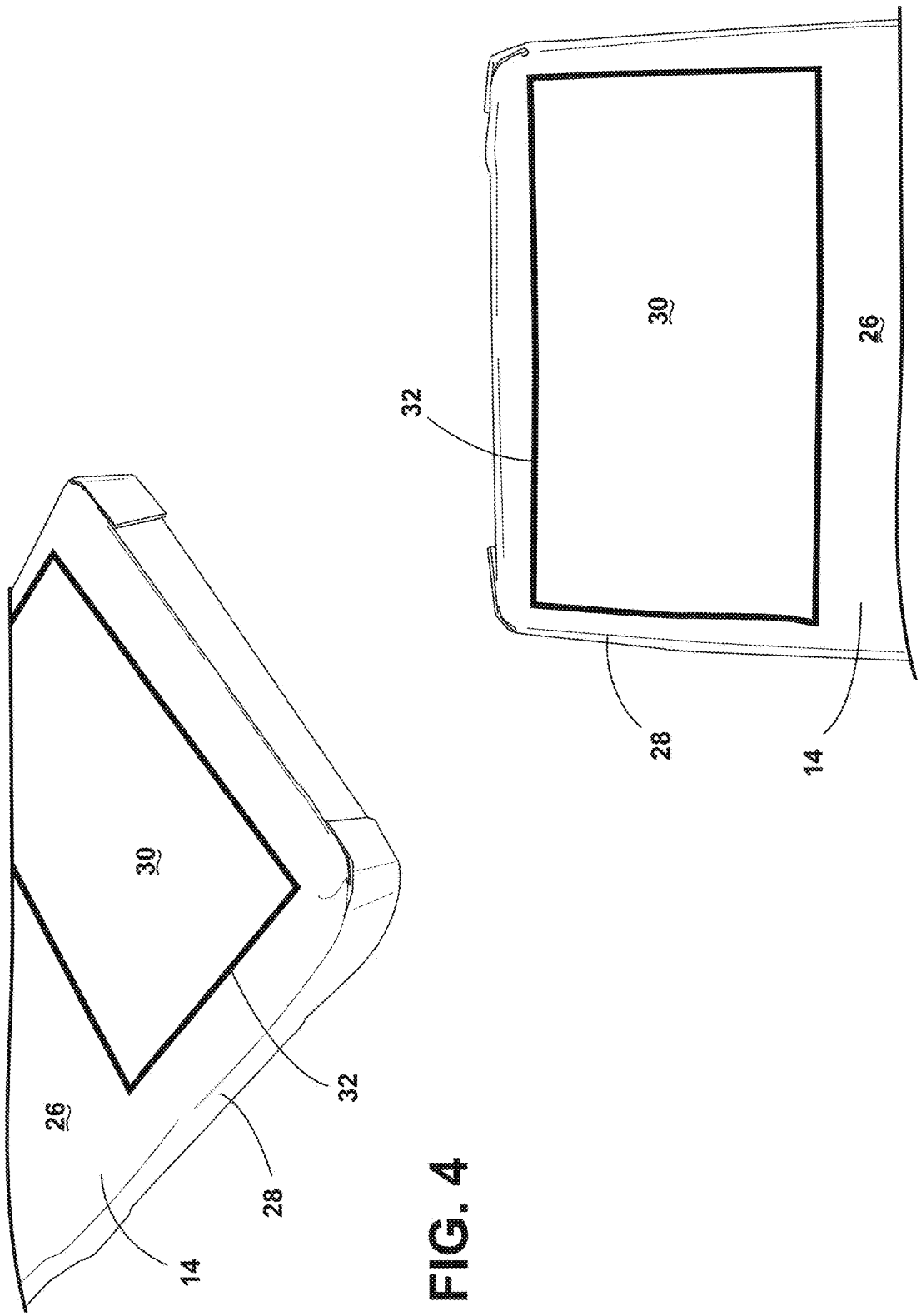

SURGICAL TABLE DISPOSABLE BASE COVER

CROSS-REFERENCE TO RELATED APPLICATION

This application claims priority to and the benefit under 35 U.S.C. § 119(e) of U.S. Provisional Application No. 62/810,073, filed on Feb. 25, 2019, entitled "SURGICAL TABLE DISPOSABLE BASE COVER," the disclosure of which is hereby incorporated herein by reference in its entirety.

FIELD OF THE DISCLOSURE

The present disclosure generally relates to a base cover to minimize contaminants on the bottom of a surgical table, and more specifically to a surgical table disposable base cover that can be easily installed and removed prior to and after a surgical event.

SUMMARY OF THE DISCLOSURE

According to one aspect of the present disclosure, a disposable base cover includes a first portion and a second portion. The first portion includes a top wall and a peripheral side wall that extends orthogonally therefrom and a side edge with a first fastening feature. The second portion includes a top wall and a peripheral side wall extending generally orthogonally therefrom and an equipment zone that provides visual indicia of equipment zone bounds. The second portion also includes a side edge with a second fastening feature that is complementary to the first fastening feature. The disposable base cover is configured for engagement with a base of a surgical table.

According to another aspect of the present disclosure, a disposable base cover includes a first portion and a second portion. The first portion includes a top wall and a peripheral side wall that extends orthogonally therefrom and a side edge with a first fastening feature. The second portion includes a top wall and a peripheral side wall that extends generally orthogonally therefrom and an equipment zone on the top wall that provides visual indicia of a boundary of the equipment zone. The second portion also includes a side edge with a second fastening feature that is complementary to the first fastening feature. A third portion generally defines a sleeve that is removably coupled with the first portion and the second portion and defines an open column configured to receive a table pedestal of the surgical table.

According to yet another aspect of the present disclosure, a disposable base cover includes a first portion and a second portion. The first portion includes a top wall and a peripheral side wall that extends orthogonally therefrom and a side edge with a first fastening feature. The second portion includes a top wall and a peripheral side wall that extends generally orthogonally therefrom and an equipment zone on the top wall that provides visual indicia of a boundary of the equipment zone. The second portion also includes a side edge with a second fastening feature that is complementary to the first fastening feature. The first portion and the second portion include an absorbent material disposed on a first side thereof and an impermeable material disposed on a second side thereof. A third portion generally defines a sleeve that is removably coupled with the first portion and the second portion and defines an open column configured to receive a table pedestal of a surgical table.

These and other features, advantages, and objects of the present invention will be further understood and appreciated by those skilled in the art by reference to the following specification, claims, and appended drawings.

BRIEF DESCRIPTION OF THE DRAWINGS

In the drawings:

FIG. 4 is a partial side perspective view of a portion of a disposable base cover of the present disclosure;

FIG. 5 is a partial top plan view of a portion of a disposable base cover of the present disclosure;

DETAILED DESCRIPTION

Figure 1:
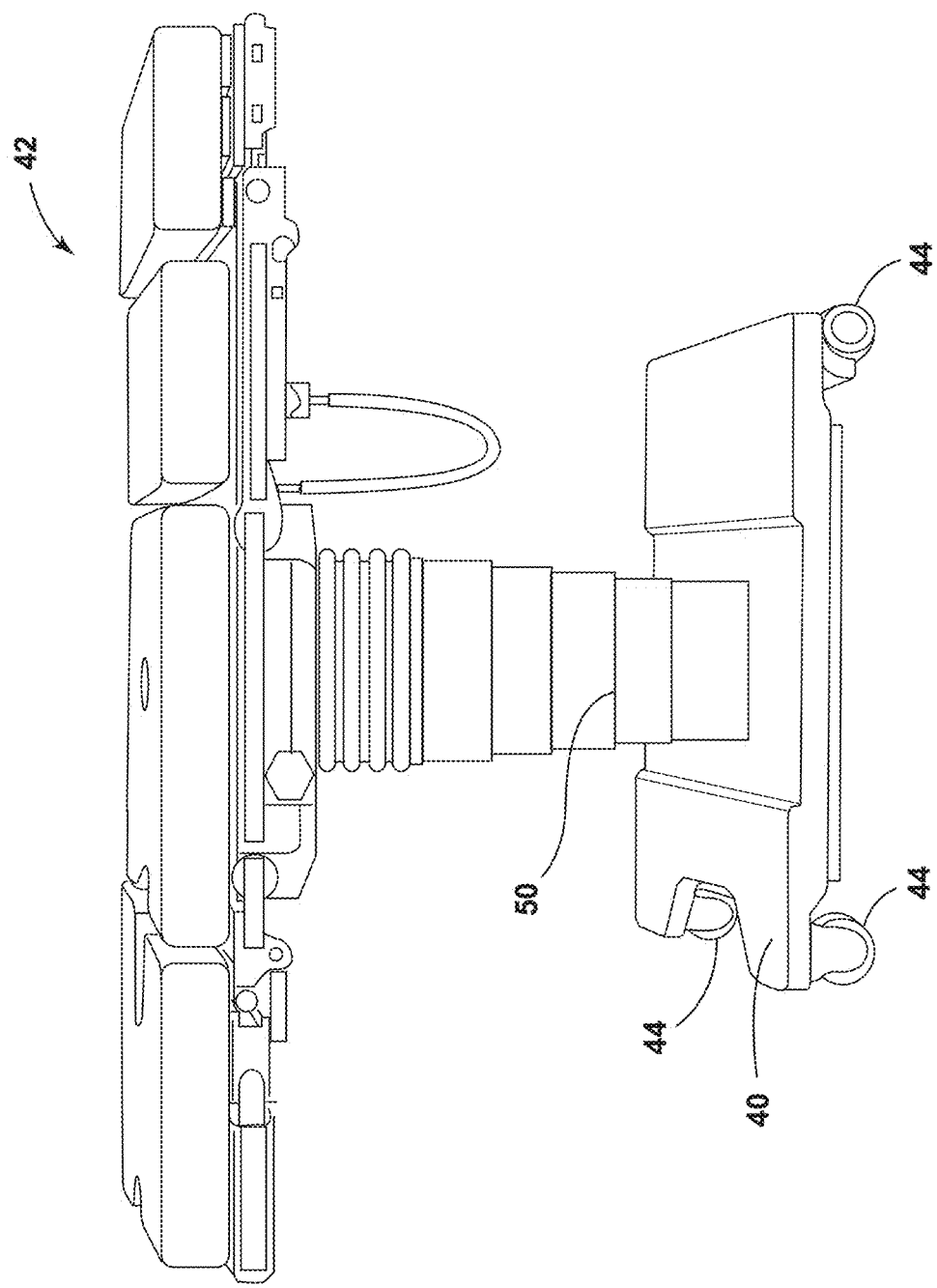
FIG. 1 is a front perspective view of a surgical table configured for use with a disposable base cover.

The present illustrated embodiments reside primarily in combinations of method steps and apparatus components related to a base cover to minimize contaminants on the bottom of a surgical table. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to the surface closer to an intended viewer, and the term "rear" shall refer to the surface further from the intended viewer. However, it is to be understood that the disclosure may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Referring to FIGS. 1-9, reference numeral 10 generally designates a disposable base cover having a first portion 12 and a second portion 14. The first portion 12 includes a top wall 16 and a peripheral side wall 18 extending orthogonally therefrom. The first portion 12 also includes a side edge 20 with a first fastening feature 22. The second portion 14 includes a top wall 26 and a peripheral side wall 28 extending generally orthogonally therefrom. The second portion 14 also includes an equipment zone 30 that provides visual indicia 32 of equipment zone bounds. The second portion 14 includes a side edge 34 with a second fastening feature 36 that is complementary to the first fastening feature 22. The disposable base cover 10 is configured for engagement with a base 40 of a surgical table 42 having rollers 44 to provide mobility to the surgical table 42.

Figure 1A:
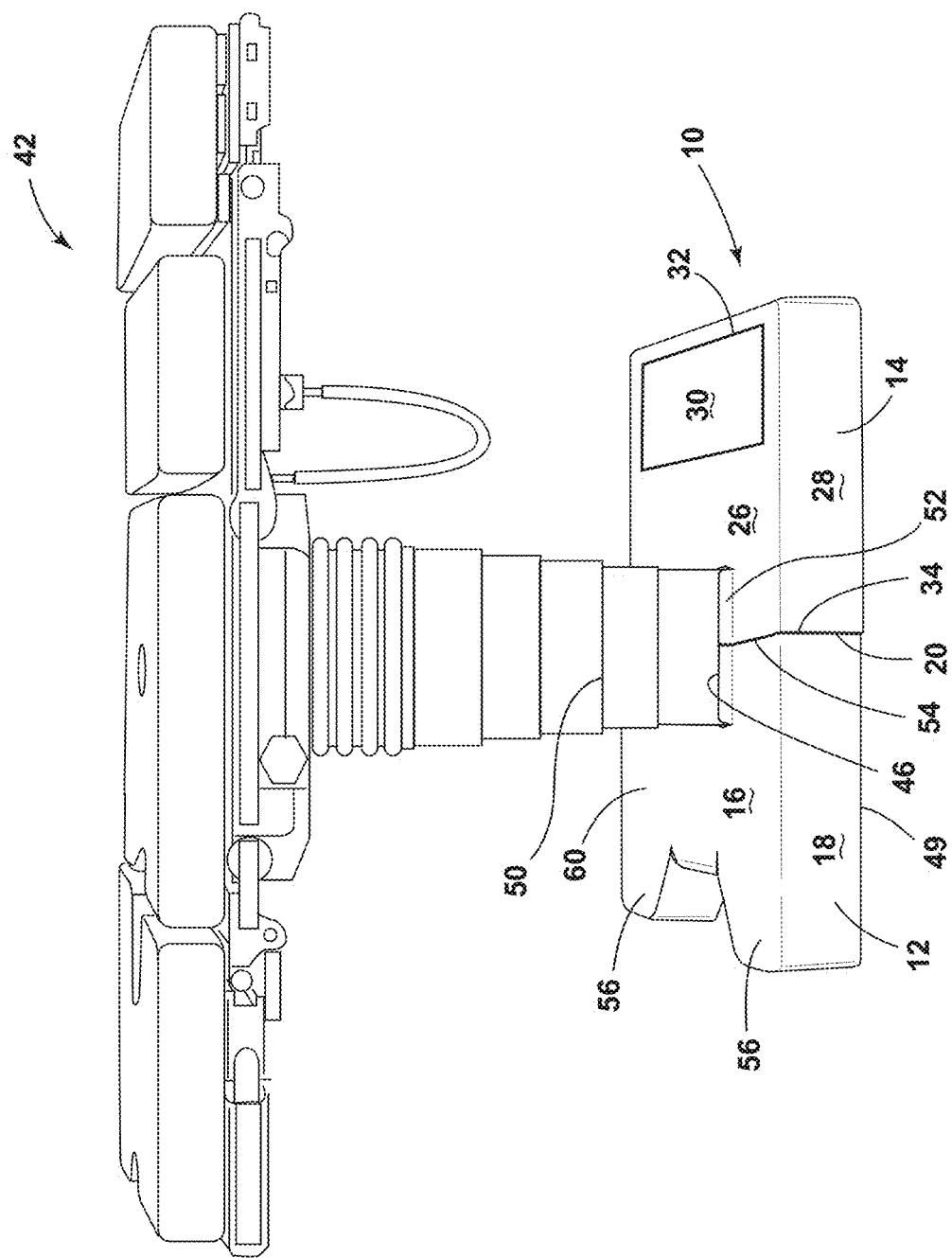
FIG. 1A depicts the surgical table of FIG. 1 with the disposable base cover installed.

With reference to FIGS. 1 and 1A, the illustrated surgical table 42 is configured to provide support to a patient during a surgical procedure. Sometimes during a surgical procedure, fluids, including body fluids, medicinal fluids, or a combination thereof may leave the surgical site, sometimes resulting in these fluids hitting the floor or the base 40 of the surgical table 42. While cleaning of the floor can be relatively easy, cleaning the base 40 of the surgical table 42 is often very difficult due to the different surfaces of the base 40. As a result, the disposable base cover 10 may be utilized to protect the base 40 of the surgical table 42 and keep the base 40 clean from fluids during surgery. The first and second portions 12, 14 of the disposable base cover 10 may include an absorbent material disposed on a first side thereof and an impermeable material disposed on a second side thereof to aid in keeping the base 40 clean from the surgical fluids. The disposable base cover 10 generally defines a central opening 46 through which a table pedestal 50 of the surgical table 42 extends. A collar 52 may be disposed about a periphery of the central opening 46. The collar 52 may extend partially onto the table pedestal 50 and cover the juncture between the base 40 and the table pedestal 50. The table pedestal 50 connects the surgical table 42 with the base 40. The collar 52 may extend vertically about the table pedestal 50 of the surgical table 42 to protect the surgical table 42 from splash or splatter of fluids. The collar 52 may have a short or tall height. A slit 54 extends from the central opening 46 to a bottom edge 49 of the disposable base cover 10. The first portion 12 of the disposable base cover 10 includes extensions 56 generally configured to cover extended portions of the base 40 of the surgical table 42 that have rollers 44. It will be understood that the extensions 56 can be replaced by a generally rectangular construction of the top wall 16 such that the first portion 12 of the disposable base cover 10 and the second portion 14 of the disposable base cover 10 are mirror images, or nearly mirror images, of one another. It will also be understood that the peripheral side wall 18 of the first portion 12 of the disposable base cover 10 may be folded and stapled, adhered, or otherwise fastened together at each of the extensions 56.

Figure 1B:
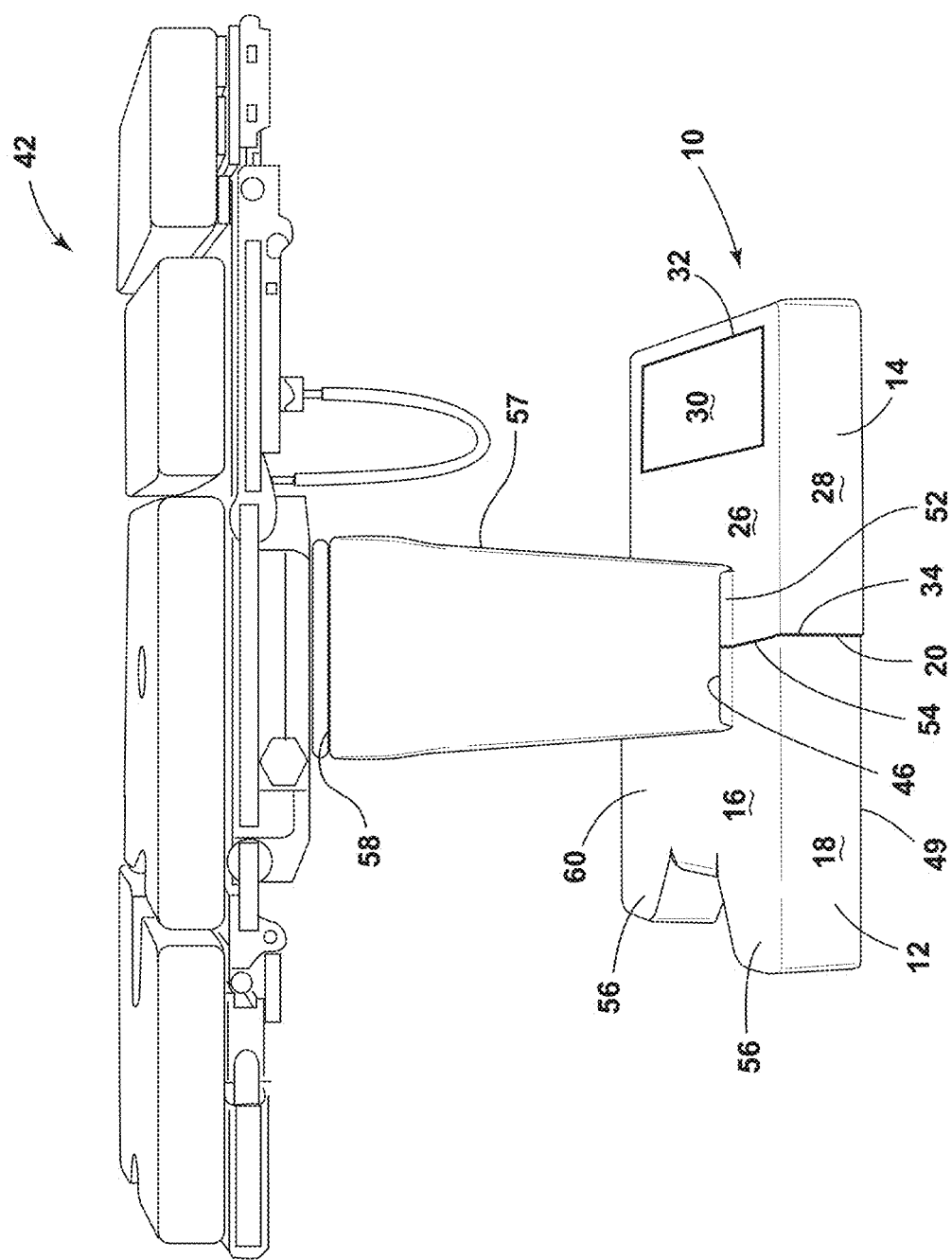
FIG. 1B depicts the surgical table of FIG. 1A with an upper sleeve installed around a table pedestal of the surgical table.

With reference now to FIG. 1B, the disposable base cover 10 may include an upper sleeve 57 configured to wrap around the table pedestal 50. The upper sleeve 57 may couple directly with the top wall 16 of the first portion 12 and the top wall 26 of the second portion 14. Alternatively, the upper sleeve 57 may engage the collar 52. The upper sleeve 57 may be flexible and stretchable and may be movable as the table pedestal 50 extends or contracts to suit the needs of a caregiver. The upper sleeve 57 may also include an upper fastening feature 58 that operably secures the upper sleeve 57 with an upper portion of the table pedestal 50. The upper fastening feature 58 may include methods for fastening by non-woven, stretchable material (such as an elastic band), or by cinch tie, hook and loop, adhesive, etc. Alternatively, the upper sleeve 57 could be attached to the disposable base cover 10 (for example, by being sewn, glued, etc.) or could extend past the central opening 46 of the disposable base cover 10 so fluids can run off the upper sleeve 57 covering the table pedestal 50 onto the disposable base cover 10. The upper sleeve 57 may be integral with the first portion 12, the second portion 14, or both of the first portion 12 and the second portion 14. It is also contemplated that the upper sleeve 57 may be operably coupled with a top surface or bottom surface of the first portion 12 and the second portion 14 at the central opening 46.

With reference now to FIGS. 4 and 5, the second portion 14 of the disposable base cover 10 includes a generally rectangular construction of the top wall 26 that includes the equipment zone 30 disposed thereon. The visual indicia 32 extends about a periphery of the equipment zone 30. It will be understood that the equipment zone 30 may be used to support equipment used during surgery, including, but not limited to equipment trays, electronic devices, sponges, surgical drapes, patient warming devices, etc. In addition, it will be understood that the equipment zone 30 may be comprised of a different material than the remainder of the disposable base cover 10, and further may include a material of high frictional resistance disposed thereon to minimize movement of objects placed on the equipment zone 30. The equipment zone 30 may also include a mild adhesive that provides a tacky surface area at the equipment zone 30. Moreover, the visual indicia 32, that defines the equipment zone 30, may include a raised surface that extends above a planar extent of the equipment zone 30 thereby minimizing the likelihood that items placed in the equipment zone 30 will roll or fall out of the equipment zone 30. The visual indicia 32 may also include a material of high friction, possibly even higher than that of the equipment zone 30, and may also include a very bright or lit boundary that clearly illustrates the bounds of the equipment zone 30. The visual indicia 32 may also include a mild adhesive that prevents or limits objects placed within the equipment zone 30 from leaving the equipment zone 30.

Figure 2:
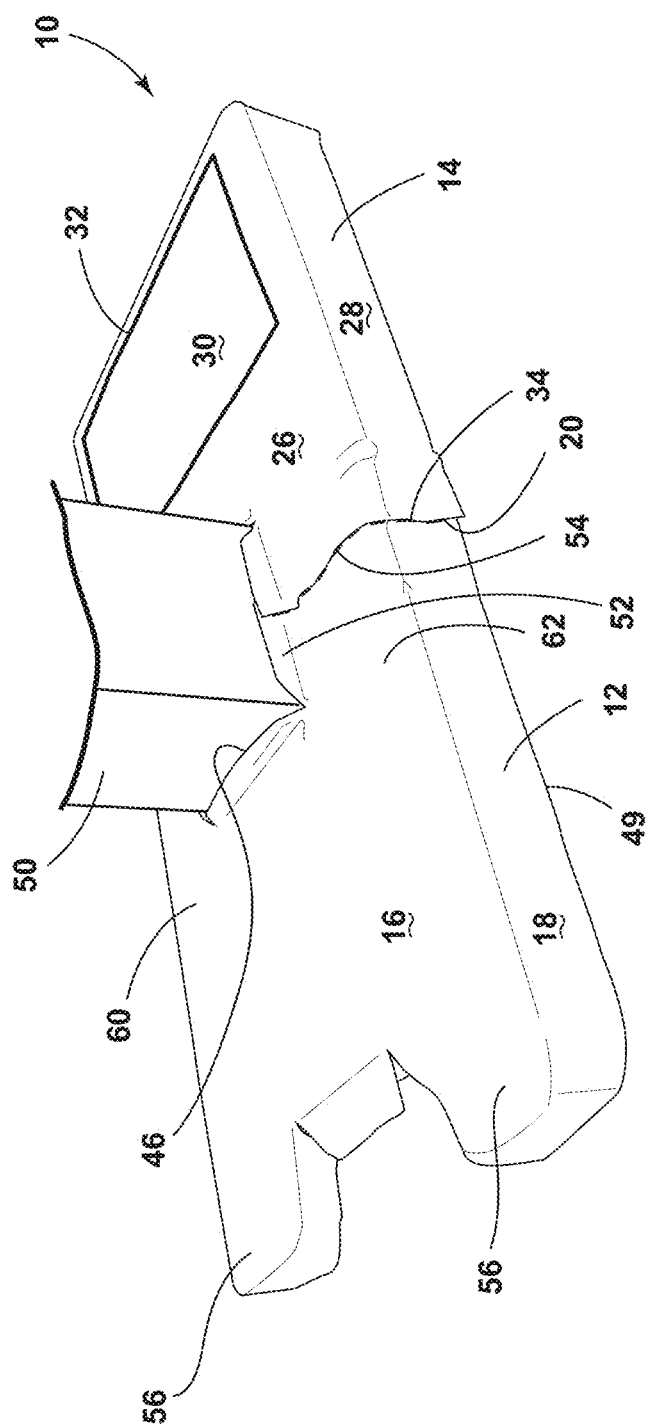
FIG. 2 is a top perspective view of a disposable base cover of the present disclosure.
Figure 3:
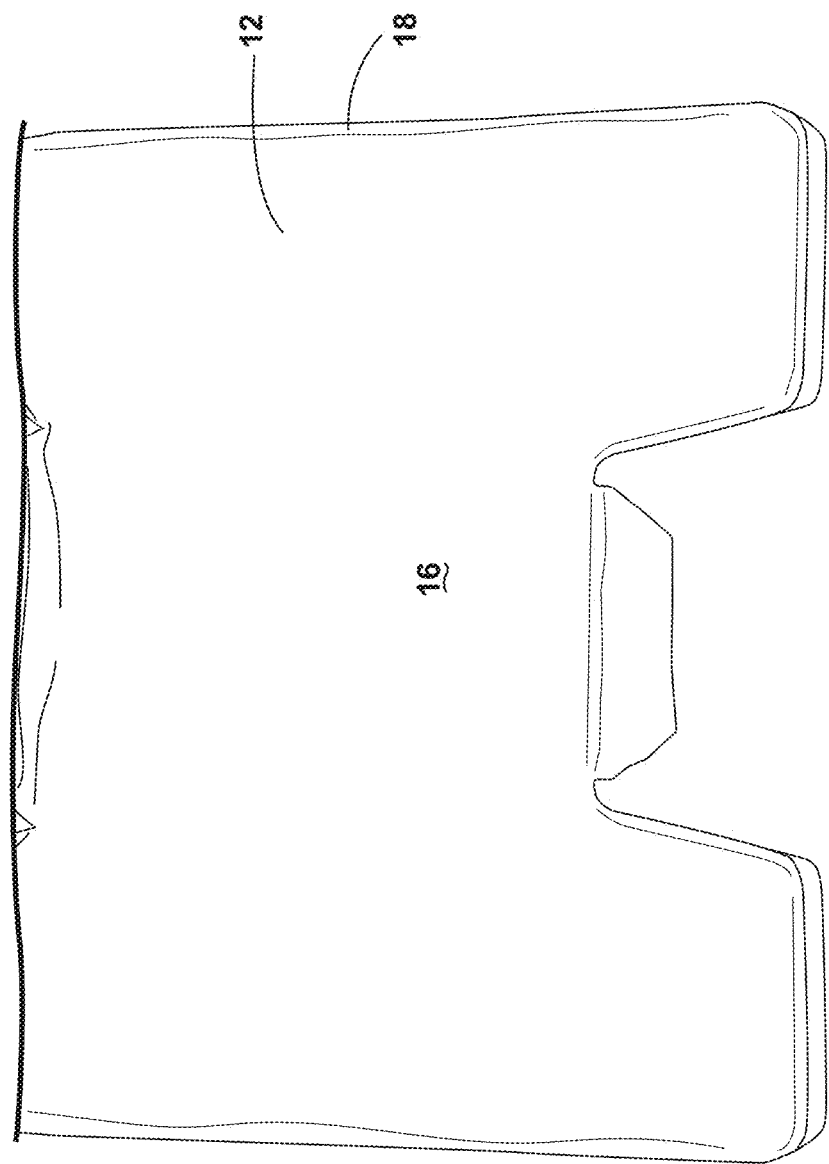
FIG. 3 is a partial top perspective view of one portion of a disposable base cover of the present disclosure.
Figure 6:
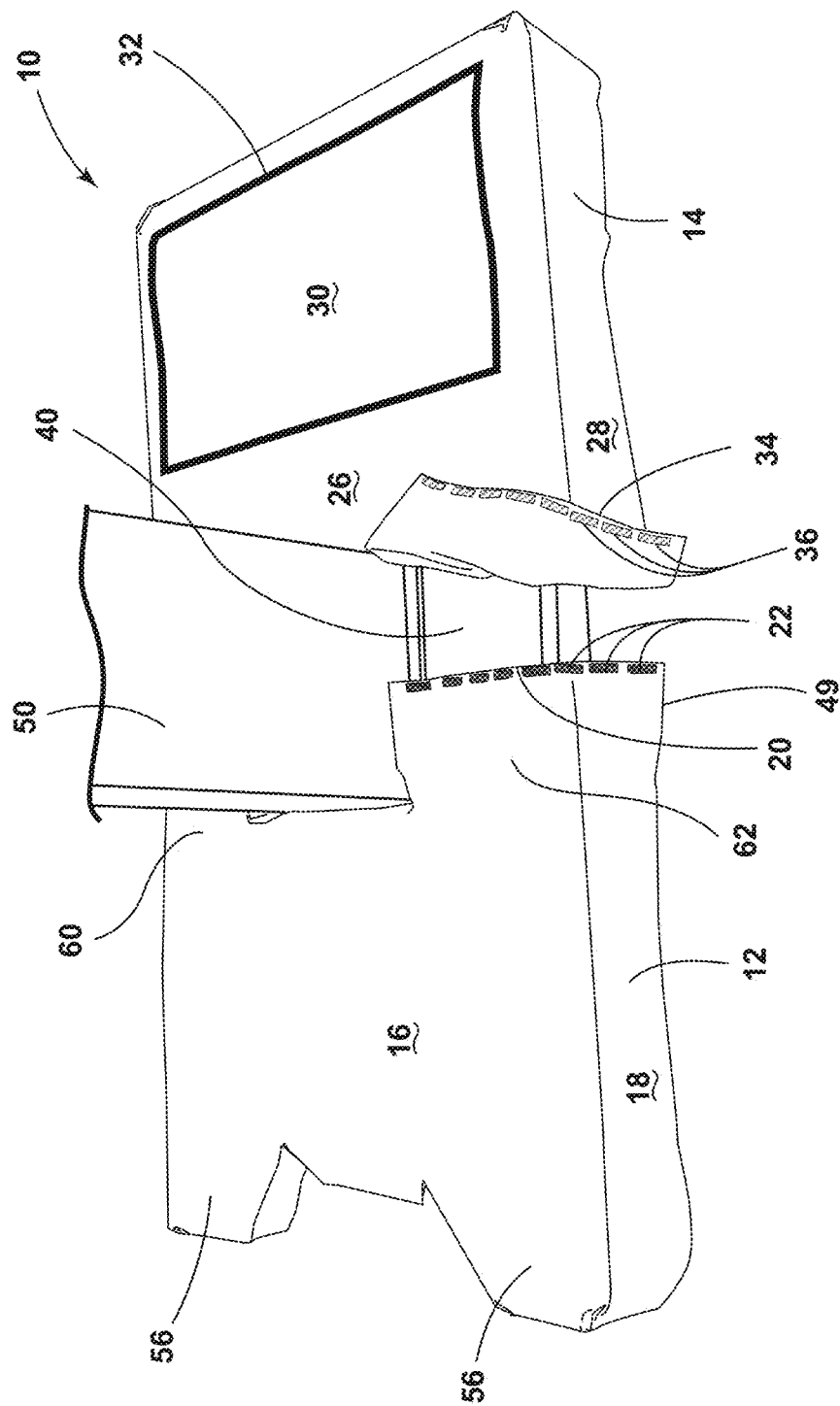
FIG. 6 is a top perspective view of a disposable base cover of the present disclosure prior to secure engagement with a base of a surgical table.

With reference now to FIGS. 2 and 6, it is generally contemplated that the disposable base cover 10 may include a single, uni-body construction with the slit 54 (FIG. 2) extending from the central opening 46 (FIG. 2) defined on one side that defines the side edge 20 of the first portion 12 and the side edge 34 of the second portion 14. Stated differently, the first portion 12 and the second portion 14 may be integrally connected on a back side 60 of the disposable base cover 10 and include the slit 54 at a front side 62 of the disposable base cover 10. Alternatively, the first portion 12 and the second portion 14 may be separated by a slit defined on the back side 60 of the disposable base cover 10 and the slit 54 defined on the front side 62 of the disposable base cover 10. The disposable base cover 10 can be installed or removed by separating the first fastening feature 22 from the second fastening feature 36 at the slit 54 (FIG. 6).

Figure 7:
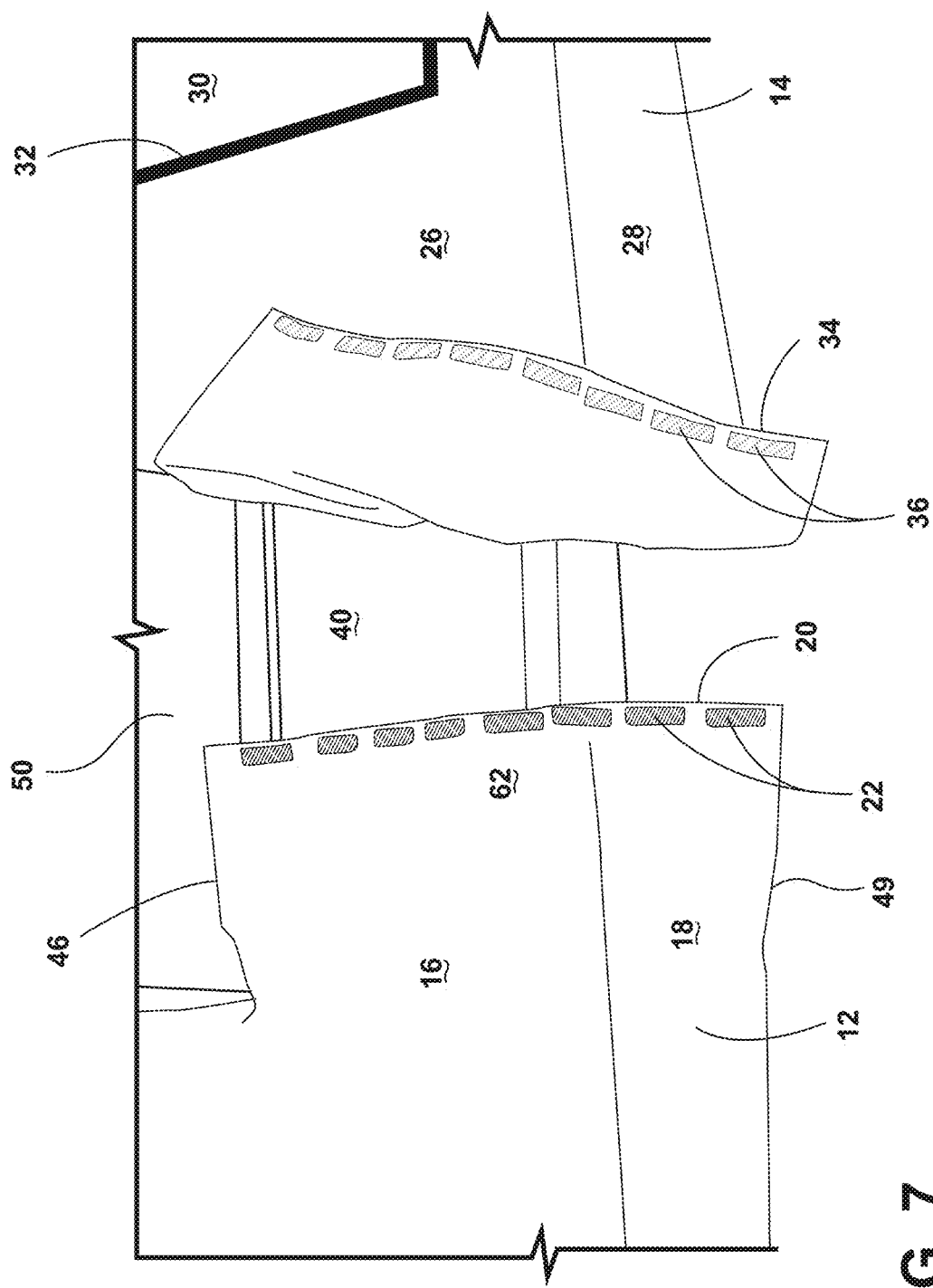
FIG. 7 is a top perspective view of fastening features of a disposable base cover of the present disclosure.

With reference now to FIG. 7, the first fastening feature 22 and the second fastening feature 36 may take on a variety of constructions. For example, the first fastening feature 22 and the second fastening feature 36 may include at least one of a plurality of hook and loop type fastening features, magnetic fastening features, adhesive fastening features, etc. Regardless, the attachment of the first and second fastening features 22, 36 is generally configured to provide a secure engagement of the side edge 20 of the first portion 12 with the side edge 34 of the second portion 14. At the same time, the secure engagement of the first and second portions 12, 14 is also easily detachable such that the disposable base cover 10 can be removed and discarded with relative ease by a person cleaning the surgical table 42. Accordingly, the base cover 10 is generally disposable.

Figure 8:
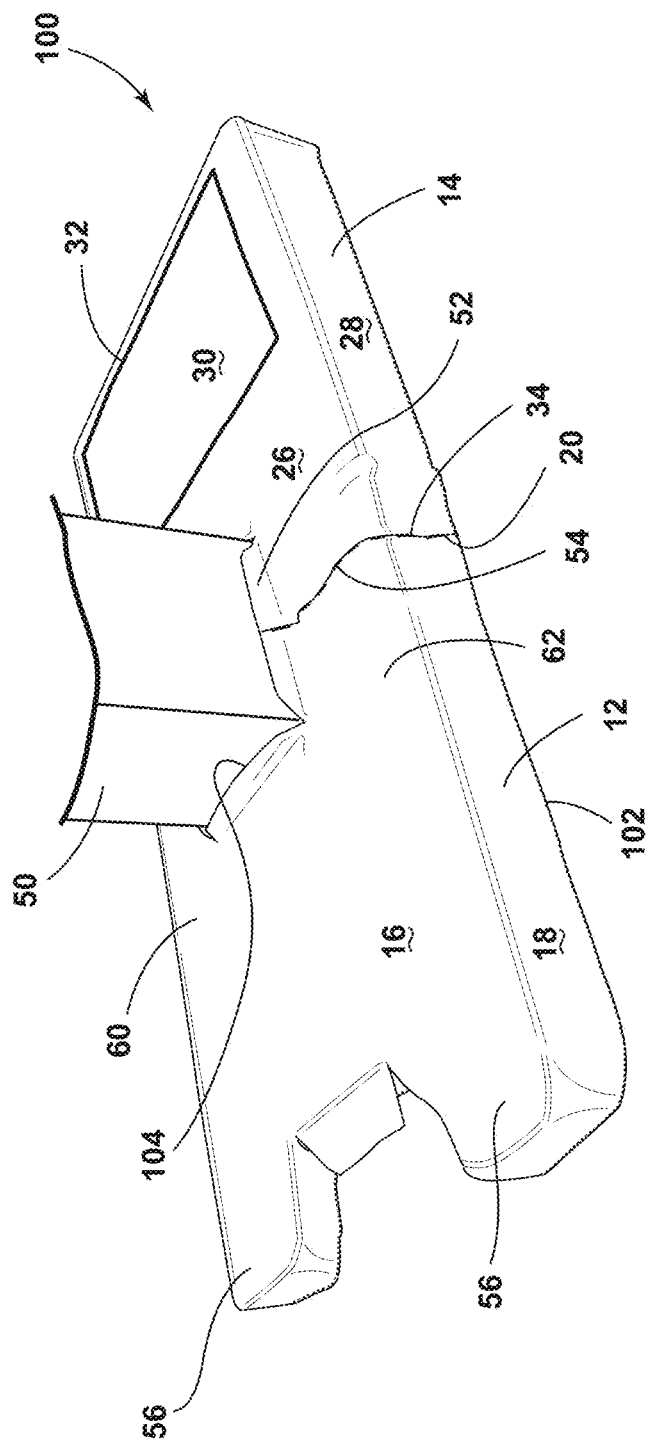
FIG. 8 is a top perspective view of another disposable base cover of the present disclosure.

With reference to FIG. 8, another aspect of the present disclosure includes a disposable base cover 100 that also includes a fitted construction. In this instance, the disposable base cover 100 may be constructed of a stretchable material having elastic qualities such that the material stretches around corners of the base 40 and the table pedestal 50 of the surgical table 42. Other features, previously disclosed, such as the equipment zone 30 and the first and second fastening features 22, 36 may also be utilized in this instance. The entire disposable base cover 100 may include elastic qualities or just areas proximate a bottom edge 102 of the disposable base cover 100 and proximate a central opening 104. It will be understood that features of the disposable base cover 100 that are similar or the same as the features of the disposable base cover 10 will include like numbers.

Figure 9:
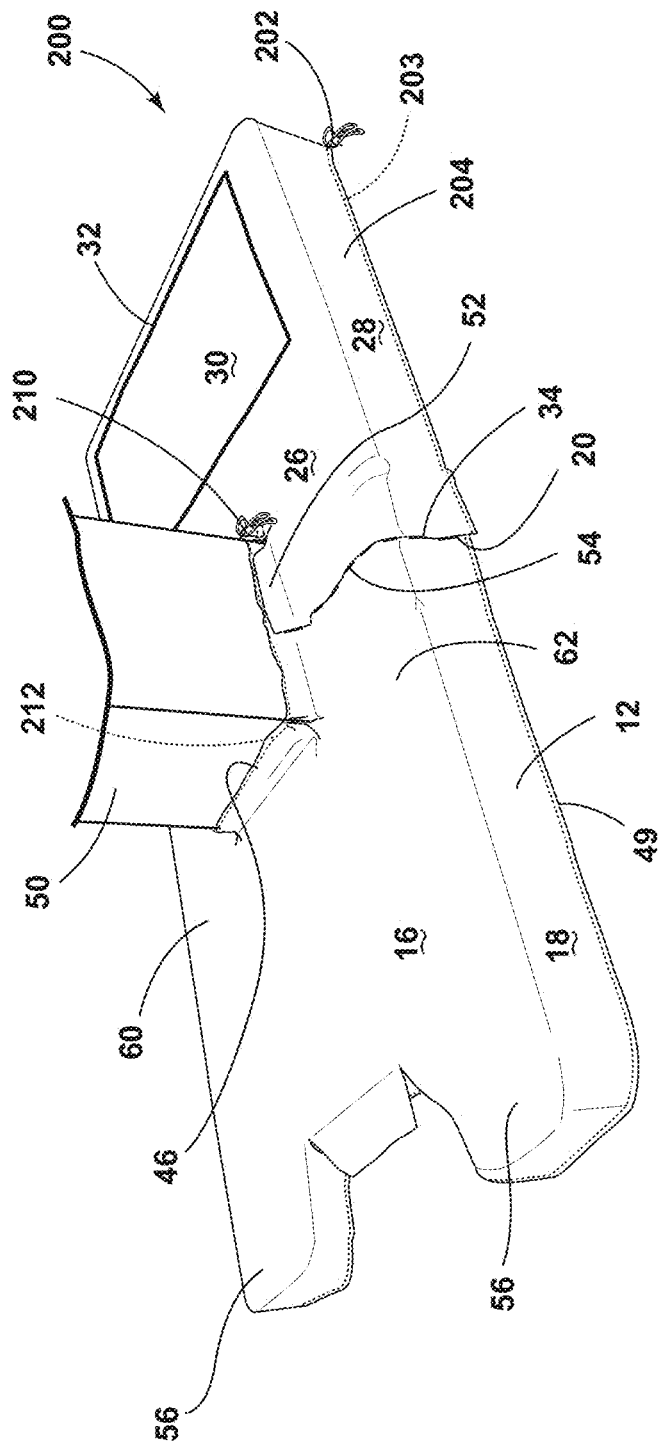
FIG. 9 is a top perspective view of another disposable base cover of the present disclosure.

With regard to FIG. 9, another aspect of the present disclosure includes a disposable base cover 200 having a cinch tie 202 that extends through a cinch channel 203. The cinch tie 202 may be configured to draw lower portions 204 of the disposable base cover 200 tight thereby minimizing exposure of the base 40 of the surgical table 42. In addition, a second cinch string 210, which extends through a cinch channel 212, may be positioned about the table pedestal 50 of the surgical table 42 to provide a snug fit between the disposable base cover 200 and the table pedestal 50. It will be understood that features of the disposable base cover 200 that are similar or the same as the features of the disposable base cover 10 will include like numbers.

The disposable base covers, as set forth herein, minimize clean up time between surgical procedures. In addition, the disposable base covers are configured for use on a host of different bases of different surgical tables, regardless of size or shape. As set forth herein, the elastic features, the cinch tie features, and fastening features, of the disposable base covers, provide a snug fit around the table pedestal thereby keeping the base of the surgical table clean. It will be understood that for the disposable base covers set forth herein, a spun-bond, non-woven drape material may be utilized. It will also be understood that the material of the disposable base covers may include hydrophilic qualities to absorb fluids or hydrophobic qualities to repel fluids away from the base 40. The disposable base covers as set forth herein may also include an absorbing layer disposed over a fluid proof material. The resulting construction absorbs fluids without allowing those fluids to penetrate through to the base 40 of the surgical table 42. The disposable base covers may extend over, and at least partially cover the rollers 44, to protect the rollers 44, or may wrap around the base 40 above the rollers 44. This material may be utilized in conjunction with an elastic material to provide flexibility. In addition, an underside of the disposable base covers may include a material of high frictional resistance to minimize movement of the disposable base covers when placed on the base 40 of the surgical table 42. It will also be understood that the construction of the disposable base covers are such that the disposable base covers do not contact a floor of a surgical suite.

Because of the ease of design and minimization of clean up resulting from the use of the disposable base covers, the base of the surgical table is better protected from biological substances and reduces the time needed to clean the surgical table before the operating room is used for the next surgical procedure. In addition, the disposable base covers require minimal time to install and minimizes operating room turnover time thereby making the surgical suite available for more time on any given day. The disposable base covers will be disposed of with other contaminated materials that are used during the surgical procedure.

According to another aspect of the present disclosure, a disposable base cover includes a first portion and a second portion. The first portion includes a top wall and a peripheral side wall that extends orthogonally therefrom and a side edge with a first fastening feature. The second portion includes a top wall and a peripheral side wall extending generally orthogonally therefrom and an equipment zone that provides visual indicia of equipment zone bounds. The second portion also includes a side edge with a second fastening feature that is complementary to the first fastening feature. The disposable base cover is configured for engagement with a base of a surgical table.

According to another aspect of the present disclosure, a first fastening feature includes an adhesive.

According to another aspect of the present disclosure, at least one of a first fastening feature and a second fastening feature is a magnetic fastening feature.

According to still another aspect of the present disclosure, a first fastening feature and a second fastening feature include a hook and fastener arrangement.

According to yet another aspect of the present disclosure, a first portion and a second portion include a stretchable material.

According to another aspect of the present disclosure, a first portion includes extensions configured to extend over rollers coupled with a base of a surgical table.

According to another aspect of the present disclosure, a first portion is attachable to a second portion. The first portion and the second portion, when attached, define a central opening through which a table pedestal extends.

According to yet another aspect of the present disclosure, a disposable base cover includes a cinch tie that extends through a cinch channel disposed at a central opening.

According to another aspect of the present disclosure, a cinch tie is constructed of a stretchable material.

According to still another aspect of the present disclosure, a first fastening feature and a second fastening feature are disposed on only one side of a surgical table support column.

According to yet another aspect of the present disclosure, a peripheral side wall of a first portion and a peripheral side wall of a second portion are configured to at least partially cover rollers coupled with a base.

According to another aspect of the present disclosure, a disposable base cover includes a first portion and a second portion. The first portion includes a top wall and a peripheral side wall that extends orthogonally therefrom and a side edge with a first fastening feature. The second portion includes a top wall and a peripheral side wall that extends generally orthogonally therefrom and an equipment zone on the top wall that provides visual indicia of a boundary of the equipment zone. The second portion also includes a side edge with a second fastening feature that is complementary to the first fastening feature. A third portion generally defines a sleeve that is removably coupled with the first portion and the second portion and defines an open column configured to receive a table pedestal of the surgical table.

According to still another aspect of the present disclosure, a disposable base cover includes a cinch tie that extends through a cinch channel disposed at an open column.

According to yet another aspect of the present disclosure still, a disposable base cover includes a first portion and a second portion. The first portion includes a top wall and a peripheral side wall that extends orthogonally therefrom and a side edge with a first fastening feature. The second portion includes a top wall and a peripheral side wall that extends generally orthogonally therefrom and an equipment zone on the top wall that provides visual indicia of a boundary of the equipment zone. The second portion also includes a side edge with a second fastening feature that is complementary to the first fastening feature. The first portion and the second portion include an absorbent material disposed on a first side thereof and an impermeable material disposed on a second side thereof. A third portion generally defines a sleeve that is removably coupled with the first portion and the second portion and defines an open column configured to receive a table pedestal of a surgical table.

According to another aspect of the present disclosure, a disposable base cover includes a collar that extends vertically about a table pedestal of a surgical table to protect the surgical table from splash or splatter of fluids.

According to yet another aspect of the present disclosure, a collar is integral with a first portion and a second portion and is configured to engage a sleeve.

According to still another aspect of the present disclosure, a disposable base cover includes at least one of a plurality of hook and loop type fastening features, magnetic fastening features, or adhesive fastening features.

According to still yet another aspect of the present disclosure, visual indicia defines an equipment zone and includes a raised surface that extends above a planar extent of the equipment zone.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

What is claimed is:

1. A disposable base cover comprising:
   a first portion including a top wall and a peripheral side wall extending orthogonally therefrom, wherein the first portion includes a side edge with a first fastening feature, wherein the first portion includes first and second extensions that project outward from the first portion and which are configured to extend over rollers coupled with a base of the surgical table;
   a second portion including a top wall and a peripheral side wall extending generally orthogonally therefrom, the second portion including an equipment zone that provides visual indicia extending about the entire periphery of the equipment zone bounds, wherein the visual indicia includes a raised surface that extends above a planar extent of the equipment zone, and wherein the second portion includes a side edge with a second fastening feature that is complementary to the first fastening feature, and wherein said disposable base cover is configured for engagement with the base of the surgical table;
   a collar that is defined by the first portion and the second portion, wherein the first portion is attachable to the second portion, and wherein the first portion and the second portion, when attached, define a central opening through which a pedestal of the surgical table extends; and
   a cinch tie that extends through a cinch channel disposed at the central opening.

2. The disposable base cover of claim 1, wherein the first fastening feature includes an adhesive.

3. The disposable base cover of claim 1, wherein at least one of the first fastening feature and the second fastening feature is a magnetic fastening feature.

4. The disposable base cover of claim 1, wherein the first fastening feature and the second fastening feature include a hook and fastener arrangement.

5. The disposable base cover of claim 1, wherein the first portion and the second portion include a stretchable material.

6. The disposable base cover of claim 1, wherein the cinch tie is constructed of a stretchable material.

7. The disposable base cover of claim 1, wherein the first fastening feature and the second fastening feature are disposed on only one side of a table pedestal.

8. The disposable base cover of claim 1, wherein the peripheral side wall of the first portion and the peripheral side wall of the second portion are configured to at least partially cover the rollers coupled with the base.

9. A disposable base cover comprising:
- a first portion including a top wall and a peripheral side wall extending orthogonally therefrom, wherein the first portion includes a side edge with a first fastening feature;
- a second portion including a top wall and a peripheral side wall extending generally orthogonally therefrom, the second portion including an equipment zone on the top wall that provides visual indicia of a boundary of the equipment zone, wherein the equipment zone includes a higher coefficient of friction than the first portion of said disposable base cover, and wherein the second portion includes a side edge with a second fastening feature that is complementary to the first fastening feature;
- a collar that is defined by the first portion and the second portion;
- a third portion generally defining a sleeve removably coupled with collar and defining an open column configured to receive a table pedestal of a surgical table; and
- a cinch tie that extends through a cinch channel disposed at the open column.

10. The disposable base cover of claim 9, wherein the first portion includes extensions configured to extend over rollers coupled with a base of the surgical table.

11. The disposable base cover of claim 9, wherein at least one of the first fastening feature and the second fastening feature is a magnetic fastening feature.

12. A disposable base cover comprising:
- a first portion including a top wall and a peripheral side wall extending orthogonally therefrom, wherein the first portion includes a side edge with a first fastening feature, wherein the first portion includes first and second extensions that project outward from the first portion and which define a trapezoidal recess therebetween, the first and second extensions being configured to extend over rollers coupled with a base of a surgical table;
- a second portion including a top wall and a peripheral side wall extending generally orthogonally therefrom, the second portion including an equipment zone on the top wall that provides visual indicia of a boundary of the equipment zone, wherein the second portion includes a side edge with a second fastening feature that is complementary to the first fastening feature, and wherein the first portion and the second portion include an absorbent material disposed on a first side thereof and an impermeable material disposed on a second side thereof; and
- a third portion generally defining a sleeve removably coupled with the first portion and the second portion and defining an open column configured to receive a table pedestal of the surgical table.

13. The disposable base cover of claim 12, further comprising:
- a collar extending vertically about the table pedestal of the surgical table to protect the surgical table from splash or splatter of fluids.

14. The disposable base cover of claim 13, wherein the collar is integral with the first portion and the second portion and is configured to engage the sleeve.

15. The disposable base cover of claim 12, further comprising:
- at least one of a plurality of hook and loop type fastening features, magnetic fastening features, or adhesive fastening features.

16. The disposable base cover of claim 12, wherein the visual indicia that defines the equipment zone includes a raised surface that extends above a planar extent of the equipment zone.

* * * * *